United States Patent [19]
Falk et al.

[11] Patent Number: 5,834,444
[45] Date of Patent: *Nov. 10, 1998

[54] HYALURONIC ACID AND SALTS THEREOF INHIBIT ARTERIAL RESTENOSIS

[75] Inventors: Rudolf Edgar Falk, Toronto; Eva Anne Turley, Winnipeg; Samuel Simon Asculai, Toronto, all of Canada

[73] Assignee: Hyal Pharmaceutical Corporation, Mississauga, Canada

[ * ] Notice: The term of this patent shall not extend beyond the expiration date of Pat. No. 5,614,506.

[21] Appl. No.: 125,398

[22] Filed: Sep. 23, 1993

Related U.S. Application Data

[63] Continuation-in-part of Ser. No. 675,908, Jul. 3, 1991, Ser. No. 838,674, Feb. 21, 1992, abandoned, Ser. No. 838,675, Feb. 21, 1992, Pat. No. 5,639,738, and Ser. No. 952,095, Sep. 28, 1992, abandoned.

[51] Int. Cl.$^6$ .......................... A61K 31/715; C08B 37/00
[52] U.S. Cl. .............................. 514/54; 514/23; 424/493; 536/53; 536/55; 536/55.1; 536/55.2; 536/55.3
[58] Field of Search ....................... 514/23, 54; 536/55.2, 536/55.3, 55, 55.1, 53

[56] References Cited

U.S. PATENT DOCUMENTS

| | | | |
|---|---|---|---|
| 4,736,024 | 4/1988 | Della Valle et al. | 536/55.3 |
| 4,808,576 | 2/1989 | Schulz et al. | 514/54 |

OTHER PUBLICATIONS

Reynolds et al (eds.) (1982) "Martindale The Extra Pharmacopoeia,"The Pharmaceutical Press, London, pp. 234–235. Months not available.

Leeson et al (1976) "Histology", W. B. Saunders Company, Philadelphia, pp. 257–273. Months not available.

Shannon et al (1980) Immunol. Commun. 9(8) 735–746, (1989). Months not available.

West et al (1989) Exp. Cell Res. 183 :179–196. Months not available.

Berk et al (1991) J. Amer. Coll. Cardiology 17(6) :111B–117B, (May Issue) Months not available.

"Stedman's Medical Dictionary", 25th Edition (1990) Williams & Wilkins Baltimore, pp. 1349 & 1473. Months not available.

Turley, E.A. et al., "Noeintimal formation after balloon catheter injury: a role of hyaluronan and hyaluronan receptor RHAMM", unpublished manuscript submitted by applicant. No months available.

Yang, B. et al., Identfication of two hyaluronan–binding domains in the hyaluronan receptor RHAMM, J. Biol. Chem. vol. 263(12) pp. 8617–8623, 1993 No months available.

*Primary Examiner*—Kathleen K. Fonda
*Attorney, Agent, or Firm*—Ivor M. Hughes; Neil H. Hughes; Marcelo K. Sarkis

[57] ABSTRACT

A method is provided of preventing arterial restenosis of an animal after the arteries have been traumatized. The method comprises the administration of a therapeutically effective non-toxic amount of hyaluronic acid and/or pharmaceutically acceptable salts thereof to the animal to prevent narrowing of the arteries. The form of hyaluronic acid is selected from hyaluronic acid and pharmaceutically acceptable salts thereof having a molecular weight less than 750,000 daltons.

10 Claims, 6 Drawing Sheets

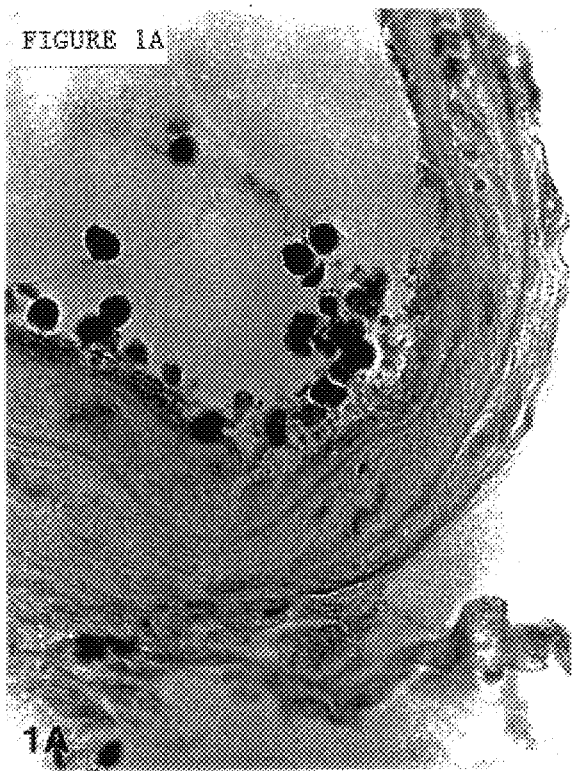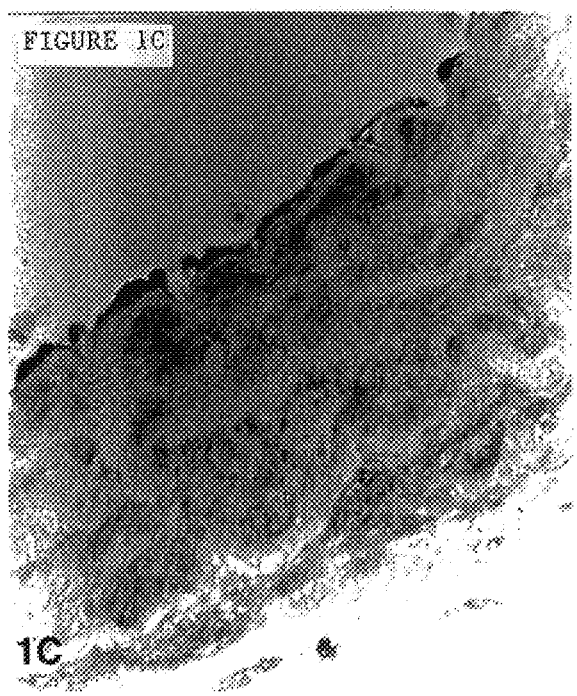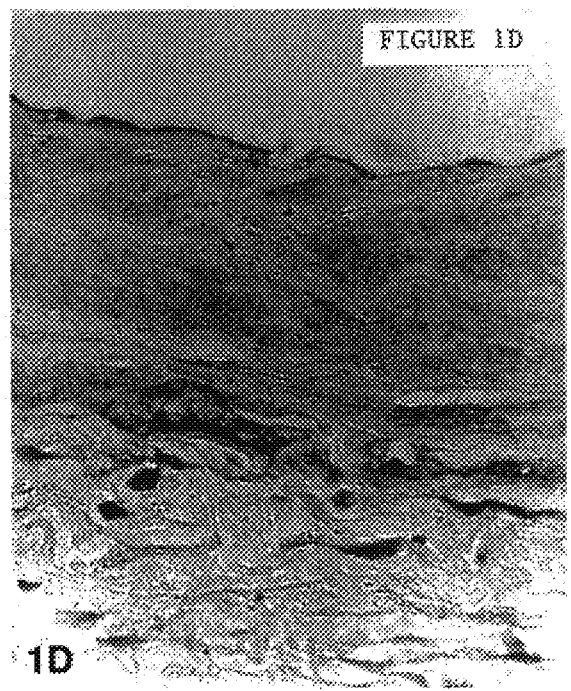

HYALURONIC ACID AND SALTS THEREOF INHIBIT ARTERIAL RESTENOSIS

This application is a continuation-in-part application of each of U.S. patent applications Ser. Nos. 07/675,908 (filed on Jul. 3, 1991), 07/838,674 (filed on Feb. 21, 1992) now abandoned, 07/838,675 (also filed Feb. 21, 1992) now U.S. Pat. No. 5,639,738, and 07/952,095 (filed Sep. 28, 1992) now abandoned, each of which is incorporated herein by reference.

FIELD OF INVENTION

This invention relates to the prevention of the narrowing (stenosis) of tubular walls of an animal after the tubular walls have been traumatized. In one embodiment, this invention relates to the prevention of arterial restenosis after balloon angioplasty.

BACKGROUND OF THE INVENTION

Balloon angioplasty is a widely accepted method of opening blockages in the coronary arteries. The balloon catheter was introduced experimentally in the early 1960's and was first applied clinically in the late 1970's. It has since assumed a major therapeutic role in the treatment of single and multiple vessel coronary artery disease (Baumgartner, H. R., 1963, Z. Ges. Exp. Med., 137:227). However in some patients after successful treatment by balloon angioplasty, arterial restenosis occurs. This time however the narrowing of the inner diameter (ID) of the artery is caused by growth (proliferation) of endothelial cells in the areas of irritation caused by the balloon angioplasty. Thus reblockage occurs not by cholesterol build-up but by build up of endothelial cells on the inner wall of the artery reducing the inner diameter (ID) of the artery leading to an infarct. In man, the restenotic lesion consists almost entirely, though not exclusively of vascular smooth muscle cells (Glazier, J. J., Williams, M. G., Madden, S. and Rickards, A. F., 1990, J. Roy. Coll. Phys. Lond., 24:292). Their accumulation within the artery lumen is a result of cell migration and proliferation. These two events are almost certainly due to the coordinated interaction of a number of different cytokines likely released by early accumulation of macrophages at the site of original tissue injury. This narrowing of the inner diameter (ID) of tubular walls or proliferation of cells is not however restricted or limited to the coronary arteries. It can also occur post operatively causing restenosis in for example peripheral vascular systems.

A number of proposals have been made in the prior art to prevent restenosis.

U.S. Pat. No. 5,087,244 (Wolinsky et al.) purports to teach the use of a catheter having an inelastic balloon at one end thereof, where the balloon has minute perforations and contains a concentrated heparin solution which will be released through the perforations contacting an area of the artery after angioplasty to prevent restenosis.

U.S. Pat. No. 5,116,864 (Hathaway et al.) purports to teach the prevention of restenosis in peripheral or cardiac vascular systems after vascular recanalisation by systemic administration of photo activatable psoralen to give serum psoralen levels which inhibit smooth muscle cell growth.

U.S. Pat. No. 5,092,841 (Spears, J. R.) purports to teach the treatment of an arterial wall injured during angioplasty by delivering bio-protective material between the wall and the angioplasty catheter so that the bio-protective material is entrapped and permeates into the tissues and vessels of the arterial wall during opposition of the angioplasty catheter.

EP 356275-A (Petitou et al.) purports to teach the use of new o-acylated glycosamino-glycan derivatives in the inhibition of post-operative restenosis.

Berk., B. C. et al in the J. Am. Coll. Cardiol. dated 1991 Vol. 17 #6 Supplement B, pp 111B–117B purports to discuss the pharmacologic roles of heparin and glucocorticoids to prevent restenosis after coronary angioplasty.

WO 9209561 (Itoh et al.) purports to teach the use of new ACAT inhibiting amide derivatives in treatment of restenosis after percutaneous transluminal coronary angioplasty.

WO 9208472 (Scarborough et al.) purports to teach the use of platelet antiadhesive peptide(s) obtained from snake venom for the prevention of restenosis following angioplasty.

WO 9207852 (Bovy et al.) purports to teach the use of certain biphenylalkyl xanthine derivatives to prevent post-angioplasty restenosis.

WO 9205782 (Pill, J.) purports to teach the use of thromboxane-A2-receptor antagonists (I) in the preparation of medicaments for inhibition of proliferative developments in obstructive vascular disorders ie. arterial restenosis.

WO 9118639 (GAj et al.) purports to teach the inhibition of stenosis after balloon angioplasty, by the administration of fibronectin by continuous or bolus infusion, or by direct infusion into the stenotic region via the angioplasty catheter.

CA 2,042,159 laid open application (Ondetti, et al.) purports to teach the use of ACE inhibitor (via the oral or parenteral route) for preventing or reducing the risk of restenosis following angioplasty.

U.S. Pat. No. 4,929,602 (Harker, et al.) purports to teach a method of inhibiting arterial restenosis by administration of D-phenyl alanyl-prolyl-arginyl-balomethyl ketone peptide derivative or a hydrolalin acid addition thereof.

U.S. Pat. No. 4,820,732 (Shell, et al.) purports to teach a composition containing a prostaglandin compound for the reduction of restenosis and abrupt stenosis.

Applicant is also aware of a company Glycomed developing a fragment of Heparin that prevents arterial restenosis after balloon angioplasty.

In the basic research efforts in the latter '70s and the early 80's, there existed considerable confusion as to what role immunotherapy should take in cancer. Activation or "hyping" of macrophages was thought to be important. However, in an examination of peritoneal macrophages obtained from patients with neoplastic disease, there was definite evidence that these macrophages were already activated yet were co-existing with cancer cells and not causing their destruction.

It has been shown by several independent investigators that the malfunction of macrophages or the putitive block is due to excessive prostaglandin and that this can be altered in tissue culture by corticosteroids, ASA, and the non-steroidal anti-inflammatory drugs, i.e. indomethacin, and naproxen (Naprosyn™). Again, in animal tumors it was repeatedly demonstrated that these substances could alter the response to neoplastic cells and that various combinations of these substances employed with immune enhancing agents could produce very credible success in eliminating experimental tumors. Researchers have combined Indomethacin therapy with Interleukin 2 and showed that this could effect a cure with experiment neoplasm.

There were continued problems with the use of any of these agents in the actual human in vivo experience. All of the non-steroidal anti-inflammatory agents (NSAID) produced major toxicity in terms of gastro-intestinal, neurological, and other areas. Thus, the basis of the present approach is that under general circumstances the use of these agents in human disease, in sufficient amounts, the drug will penetrate to any pathological tissue to alter therapeutically local prostaglandin production. While intravenous preparations exist of Indomethacin and now of other agents, the data is overwhelming, that using these drugs alone produces prohibitive side effects in human subjects. Therefore only insufficient amounts can be brought into the body to effect more than occasional responses in neoplasm.

However the majority of the evidence is present to indicate and therefore it can be postulated that the basis for neoplastic development and how the initial cell "sneaks by" the immune surveillance mechanism relates to its production of prostaglandin. One need postulate only one mutation to alter the amount of prostaglandin synthesis produced by cells when they become "malignant" to establish a mechanism of blocking out the initial cell in any immune reaction, i.e. the macrophage. It therefore became essential to develop a combination of NSAIDS for clinical use to produce a major improvement in response in neoplastic disease and other conditions where excessive prostaglandin synthesis represents the basis of the pathogenesis of this disease state, i.e. arthritis, and various others of the so-called connective tissue inflammatory disorders and/or auto-aggressive diseases.

It is therefore an object of this invention to provide a method of treatment and formulations and pharmaceutical compositions for preventing arterial restenosis after for example balloon angioplasty when endothelial cell proliferation occurs on the inner arterial wall caused by irritation to the cells by balloon angioplasty.

It is a further object of the invention to provide such treatment using hyaluronic acid which is safe and essentially non-toxic.

It is a further object of the invention to provide methods of treatment and formulations and pharmaceutical compositions generally for preventing restenosis and inhibiting restenosis for example post operatively in peripheral vascular systems.

Further and other objects of the invention will be realized by persons skilled in the art from the following summary of the invention and discussion with respect thereto.

SUMMARY OF THE INVENTION

Applicants believe that forms of hyaluronan or hyaluronic acid (especially hyaluronic acid and salts thereof) will prevent stenosis of the inner diameter (ID) of irritated tubular walls and particularly prevent restenosis of the arterial walls by for example the proliferation of endothelial cells as a result of irritation arising from balloon angioplasty or other treatment. The forms of hyaluronic acid (for example hyaluronic acid and salts of hyaluronic acid) can be administered intravenously or by injection (in the case of direct injection of small amounts) in effective amounts of about 10 mg/70 kg person to in excess of 3000 mg/70 kg person prior to, during and/or after injury.

Hyaluronan or hyaluronic acid is a glycosaminoglycan that is evolutionarily conserved and composed of repeating dissacharide units of N-acetyl-glucosamine and glucuronic acid (Laurent and Fraser, 1991, Faseb J., 6:2397). Hyaluronan exerts effects on cell adhesion, motility, growth and differentiation and many of these effects are mediated by the expression of hyaluronan receptors by responding tissues. Thus, hyaluronan was shown to be able to aggregate white cells as a result of its interaction with receptors present on these cells (review, Turley, E. A., 1992, Can, Met. Rev., 11:21). Hyaluronan accumulates almost exclusively at sites of increased receptor expression or in the presence of extracellular hyaluronan binding proteins. Two cell surface associated receptors have been molecularly characterized and include CD44 and RHAMM [Receptor for (Hyaluronan) HA—Mediate Motility]. RHAMM is present in elevated amounts on cells, particularly macrophages and smooth muscle cells responding to injury.

Therefore according to one aspect of the invention, there is provided a process for the prevention of the narrowing of the tubular walls of an animal after the tubular walls have been traumatized (for example wherein the tubular walls are arteries which have been subjected to balloon angioplasty) the process comprising the administration of a therapeutically effective non-toxic amount of hyaluronic acid and/or salts thereof and/or homologues, analogues, derivatives, complexes, esters, fragments and subunits of hyaluronic acid to the animal to prevent narrowing of the tubular walls. (The hyaluronic acid may be administered before, during and/or after the injury). Preferably the form of hyaluronic acid is hyaluronic acid and salts thereof. The amount of the form of hyaluronic acid administered is preferably between about 10 mg/70 kg person and about 3000 mg/70 kg person.

Thus according to another aspect of the invention, a process is provided for the prevention of arterial restenosis after balloon angioplasty in a human, the process comprising the administration of a therapeutically effective non-toxic amount of hyaluronic acid and/or salts thereof and/or homologues, analogues, derivatives, complexes, esters, fragments, and subunits of hyaluronic acid to the human to prevent arterial restenosis. Once again preferably the form of hyaluronan or hyaluronic acid is hyaluronic acid and salts thereof and preferably the amount of the form of hyaluronic acid administered is between about 10 mg/70 kg person and about 3000 mg/70 kg person. The hyaluronic acid can be administered before the procedure, for example, balloon angioplasty or during or after the procedure (immediately following).

The compositions are preferably administered intravenously in a liquid form and include suitable diluents or other adjuvants as required for administration. With respect to the amounts to be administered, they may also be administered by injection preferably at or proximate the site to be treated.

A therapeutically effective amount of stenosis inhibiting drug may be combined with the form of hyaluronic acid for administration. Such drugs may comprise any of those previously mentioned, and those understood by persons skilled in the art. One such drug is heparin. Another is a fragment of heparin.

A therapeutically effective amount of a non-steroidal anti-inflammatory drug (NSAID) for enhancing the effect of the form of hyaluronic acid administered in the prevention of the narrowing of the tubular walls may be administered with the form of the hyaluronic acid. The addition of the non-steroidal anti-inflammatory agent will enhance the activity of the hyaluronic acid in preventing the narrowing of the tubular walls for example enhancing the arterial restenosis prevention effect of the administered hyaluronic acid and/or salts thereof for example by reducing inflammation. The NSAID may be an NSAID suitable for the purposes and may comprise Diclofenac, Indomethacin (solubilized in for example N-Methyl Glucamine), Piroxicam, the (±) tromethamine salt of Ketorolac, acetylsalicylic acid, Naproxen and the like. The amounts of NSAID may be appropriate accepted doses preferably administered to patients. In some cases dose amounts up to 10 mg of the NSAID/kg of body weight (for example 1–2 mg of NSAID/kg of body weight) are suitable. With Diclofenac much larger amounts are appropriate. Where greater than normal amounts of NSAIDS are used, in order to reduce side effects caused by excess NSAID administration, greater than about 200 mg of the form of Hyaluronan or Hyaluronic Acid (HA) per 70 kg person may be administered to reduce and eliminate the side effects such as gastro-intestinal distress, neurological abnormalities, depression, etc., of administration of the NSAID.

A therapeutically effective amount of a free radical scavenger and anti-oxidant such as Vitamin C may also be added to the composition to enhance the effect of the Hyaluronic Acid and Hyaluronan administered. Such amount may be up to 50 grams—100 grams in a dosage as Vitamin C is soluble and is excreted by the kidneys although much lower amounts are normally used. Other anti-oxidants and free radical scavengers may also be used. In one embodiment the composition comprises a form of hyaluronic acid, specifically preferred hyaluronic acid and/or salts thereof, an NSAID, a stenosis inhibiting drug and/or Vitamin C for administration for the prevention of the narrowing of the tubular walls (for example the prevention of arterial restenosis after balloon angioplasty). The composition may comprise a plurality of dosage amounts from which one dosage amount may be withdrawn and used, each dosage amount containing an effective amount of each of the constituents.

Thus according to another aspect of the invention, the use of a pharmaceutical composition for the prevention of the narrowing of the tubular walls of an animal or human after the tubular walls have been traumatized is provided, the use being of a pharmaceutical composition comprising a therapeutically effective non-toxic amount of hyaluronic acid and/or salts thereof and/or homologues, analogues, derivatives, complexes, esters, fragments, and subunits of hyaluronic acid in association with a suitable diluent or pharmaceutically acceptable carrier or other adjuvants to prevent narrowing of the tubular walls—in one embodiment being administered just before the trauma and in another, immediately after the trauma. Preferably the form of hyaluronic acid or hyaluronan is hyaluronic acid and salts thereof, for example sodium hyaluronate.

According to another aspect of the invention, the use of a pharmaceutical composition for the prevention of arterial restenosis after balloon angioplasty in a human is provided, the use being of a pharmaceutical composition comprising a therapeutically effective non-toxic amount of hyaluronic acid and/or salts and/or homologues, analogues, derivatives, complexes, esters, fragments, and subunits of hyaluronic acid in association with a suitable diluent, pharmaceutically acceptable carrier or other adjuvants to prevent arterial restenosis preferably the form of hyaluronic acid is selected from hyaluronic acid and salts thereof and the amount of the form of hyaluronic acid is between about 10 mg/70 kg person and about 3000 mg/70 kg person.

In one embodiment the form of the pharmaceutical composition is for intravenous administration and is administered immediately before the trauma (for example before balloon angioplasty). In another, the composition is administered immediately after the trauma.

According to still another aspect of the invention, the pharmaceutical composition comprises a therapeutically effective amount of non-steroidal anti-inflammatory drug (NSAID) for example Diclofenac, Indomethacin (solubilized in N-Methyl Glucamine), Piroxicam, the (±) tromethamine salt of Ketorolac, acetylsalicylic acid and the like for enhancing the effect of the form of hyaluronic acid in the prevention of the narrowing of the tubular walls.

Thus according to another aspect of the invention, the use of a pharmaceutical composition for the prevention of arterial restenosis after balloon angioplasty is provided, the use being of a pharmaceutical composition comprising a therapeutically effective non-toxic amount of hyaluronic acid and/or salts thereof in association with a suitable diluent or pharmaceutically acceptable carrier or other adjuvants to prevent arterial restenosis (by administration for example intravenously of the composition). In some embodiments the amount of the hyaluronic acid and/or salts thereof is between about 10 mg/70 kg person and about 3000 mg/70 kg person. The composition may further comprise a therapeutically effective amount of a non-steroidal anti-inflammatory drug (NSAID) for enhancing the arterial restenosis prevention effect of the administered hyaluronic acid and/or salts thereof administered. The NSAID may be at accepted appropriate doses depending on the NSAID for example up to about 10 mg/70 kg of body weight (for example 1–2 mg of NSAID/kg of body weight). The appropriate dose for Diclofenac is much greater. Where it is desired to use a dose excess of NSAID, the amount of hyaluronic acid and salts thereof preferably exceeds about 200 mg/70 kg person.

The composition may further comprise a therapeutically effective amount of Vitamin C or other free radical scavenger or anit-oxidant for enhancing the effects of the form of hyaluronic acid to prevent narrowing of the tubular walls. The Vitamin C may be used in large amounts (for example even 50–100 grams) although much smaller amounts are suitable.

The composition may also comprise an effective amount of a stenosis inhibiting drug.

The composition may comprise hyaluronan or hyaluronic acid and at least of one of an NSAID, Vitamin C, free radical scavenger, anti-oxidant and stenosis inhibiting drug.

According to another aspect of the invention the use of:
an effective non-toxic amount of hyaluronic acid and/or salts thereof and/or homologues, analogues, derivatives, complexes, esters, fragments, and subunits of hyaluronic acid, in the manufacture of a pharmaceutical composition is provided for preventing the narrowing of the tubular walls of an animal after the tubular walls have been traumatized, the use being characterized by a therapeutically effective non-toxic amount of hyaluronic acid and/or salts thereof and/or homologues, analogues, derivatives, complexes, esters, fragments, and subunits of hyaluronic acid being incorporated into the pharmaceutical composition and being sufficient and effective to prevent the narrowing of the tubular walls which were traumatized as for example the arteries being damaged after balloon angioplasty. Preferably the form of hyaluronic acid is hyaluronic acid and/or salts thereof and the composition is in a liquid form. Preferably, the form of hyaluronic acid is utilized at a dose between about 10 mg to about 3000 mg/70 kg person and more preferably the form of hyaluronic acid is utilized at a dose greater than 200 mg/70 kg person. The composition may comprise a plurality of dosage amounts.

In one embodiment the pharmaceutical composition is for prevention of arterial restenosis after balloon angioplasty in humans. In embodiments the pharmaceutical composition is given before the balloon angioplasty and immediately after the trauma.

According to another aspect of the invention, the use of;

(1) hyaluronic acid and/or salts thereof and/or homologues, analogues, derivatives, complexes, esters, fragments, and subunits of hyaluronic acid, and (2) an agent selected from a non-steroidal anti-inflammatory drug (NSAID), a stenosis inhibiting drug, and Vitamin C, free radical scavenger and anti-oxidant and combinations thereof is provided in the manufacture of a pharmaceutical composition (including diluents, adjuvants and other carriers) for preventing the narrowing of the tubular walls of an animal after the tubular walls have been traumatized wherein a therapeutically effective amount of the hyaluronic acid and/or salts thereof and/or homologues, analogues, derivatives, complexes, esters, fragments, and subunits of hyaluronic acid is administered to humans together with a therapeutically effective amount of the agent (2), the use being characterized in that the amount of component (1) is an effective amount to prevent the narrowing of the tubular walls of the animal and component (2) enhances the effect of component (1) in the prevention of the narrowing of the tubular walls. Once again the pharmaceutical composition may comprise a plurality of dosage forms from which one dosage amount may be taken.

Preferably component (1) is hyaluronic acid and/or salts thereof and the composition is in a liquid form (for example for intravenous use or injection). Preferably component (1) is utilized at a dose between about 10 mg to about 3000 mg/70 kg person. In one use, component (1) is utilized at a dose greater than 200 mg/70 kg person.

Component 2 is utilized at amounts effective to enhance the effect of Component 1. Vitamin C may be utilized in amounts up to 50–100 grams per dose although much smaller amounts are more desirable. The NSAID can be administered in normally acceptable dose amounts depending on the NSAID. With some NSAIDS the amounts are 1–2 mg of NSAID per Kg of body weight, in others up to about 10 mg per kg bodyweight and in others such as Diclofenac, much larger amounts. Where the NSAID is used in dose excesses (greater amounts than the normally acceptable dose amounts, the amount of the form of hyaluronic acid preferably exceeds about 200 mg per 70 kg person. Suitable NSAIDS include Diclofenac, Piroxicam, Indomethacin (solubilized in N-methyl glucamine), acetylsalicylic acid, ±tromethamine salt of Ketorolac, naproxen and the like.

According to another aspect of the invention a pharmaceutical composition is provided comprising (together with diluents as required) an effective non-toxic amount of hyaluronic acid and/or salts thereof and/or homologues, analogues, derivatives, complexes, esters, fragments, and subunits of hyaluronic acid, for preventing the narrowing of the tubular walls of a human after the tubular walls have been traumatized, the composition being characterized by an effective non-toxic amount of hyaluronic acid and/or salts thereof and/or homologues, analogues, derivatives, complexes, esters, fragments, and subunits of hyaluronic acid being incorporated into the pharmaceutical composition to prevent the narrowing of the tubular walls. Preferably the form of hyaluronic acid is hyaluronic acid and/or salts thereof and preferably the composition is in a liquid form (such as an intraveneous (I.V.) form in an I.V. bag with diluents and pharmaceutically acceptable carriers and adjuvants). The form of hyaluronic acid may be utilized at doses between about 10 mg to about 3000 mg/70 kg person or more and in one embodiment the form of hyaluronic acid is utilized at a dose greater than 200 mg/70 kg person (especially where dosage excesses of NSAIDS are employed). In one embodiment the pharmaceutical composition is for prevention of arterial restenosis after balloon angioplasty in humans. The composition may be administered before the balloon angioplasty and/or after. The pharmaceutical composition may comprise a plurality of dosage amounts from which each dosage amount may be taken.

According to another aspect of the invention, a pharmaceutical composition is provided comprising (together with diluents, adjuvants and other pharmaceutically acceptable carriers as and if desired);

(1) hyaluronic acid and/or salts thereof and/or homologues, analogues, derivatives, complexes, esters, fragments, and subunits of hyaluronic acid, and (2) an agent selected from a non-steroidal anti-inflammatory drug, a stenosis inhibiting drug, Vitamin C, an anti-oxidant and free radical scavenger and combinations thereof for preventing the narrowing of the tubular walls of an animal after the tubular walls have been traumatized, the composition being characterized by an effective non-toxic amount of hyaluronic acid and/or salts thereof and/or homologues, analogues, derivatives, complexes, esters, fragments, and subunits of hyaluronic acid being incorporated into the composition together with a therapeutically effective amount of the agent (2), to prevent the tubular walls from narrowing, the composition being characterized that the amount of component (1) is an effective amount to prevent the narrowing of the tubular walls of the animal and the amount of component (2) enhances the effect of component (1) in the prevention of the narrowing of the tubular walls. Preferably component (1) is hyaluronic acid and/or salts thereof most preferably sodium hyaluronate and preferably in a liquid dosage form such as an Intravenous form (I.V. Bag). The composition may be made in bulk and subsequently put into individual dosage amounts. The composition may be packaged such that a plurality of dosage amounts are carried in a container (storage container or reservoir) from which each dosage amount may be withdrawn when needed for use. In some embodiments component (1) may be utilized at a dose between about 10 mg to about 1000 mg/70 kg person. In others the dose amounts may be up to 3000 mg/70 kg person or more. Preferably component (1) is utilized at a dose greater than 200 mg/70 kg person where dose excesses of the NSAID of component (2) are utilized. In one embodiment the pharmaceutical composition is for prevention of arterial restenosis after balloon angioplasty in humans and may be administered before, during and/or after the treatment.

Component 2 is utilized at amounts effective to enhance the effect of Component 1. Vitamin C may be utilized in amounts up to 50–100 grams per dose. The NSAID can be administered in appropriate dose amounts depending on the NSAID and if given in excess amounts the amount of the form of hyaluronic acid preferably exceeds about 200 mg per 70 kg person. Suitable NSAIDS are Diclofenac, Piroxicam, Indomethacin (solubilized in N-methyl glucamine), acetylsalicylic acid, ±tromethamine salt of Ketorolac, naproxen and the like.

When the composition comprises an agent selected from NSAID, stenosis inhibiting drug, Vitamin C, free radical scavenger and anti-oxidant and combinations thereof, Applicants postulate that the hyaluronic acid and/or salts thereof and/or the homologues, analogues, derivatives, complexes, esters, fragments, and/or sub units of hyaluronic acid also facilitates the transport of the agent to the site of irritation to enable the agent to penetrate the cells (in the artery, endothelial cells) which together will help prevent for example arterial restenosis.

By way of example and to illustrate the facilitation of the delivery or transport of a chemical to a site in a mammal, when ethyl alcohol is injected directly into a cancer tumor, and sonographic (ultrasound) assessment is made, it is not dispersed throughout the tumor. When the ethyl alcohol to be administered into a tumor is carried by hyaluronic acid and/or salts thereof, sonographic assessment of the tumor, demonstrates the dispersion of the ethyl alcohol throughout the tumor.

While Applicants postulate that the hyaluronic acid facilitates the transport and delivery, Applicants' invention may be used as described irrespective of the actual method of operation of the hyaluronic acid and/or salts thereof and/or the homologues, analogues, derivatives, complexes, esters, fragments and sub units of hyaluronic acid with the NSAID, stenosis inhibiting drug, Vitamin C, free radical scavenger, and/or anti-oxidant.

The combination of hyaluronic acid and salts thereof and other forms with different chemicals and drugs (for example Vitamin C, NSAIDS, stenosis inhibiting drug, etc.) alters their distribution and performance in the human body and produces an unusual targeting for underperfused tissue and/or pathological tissue. In this regard the use of ascorbic acid (Vitamin C) as a free radical scavenger (50 gm daily—1000 times the daily dose in therapeutic purposes as a Vitamin) administered intravenously with 300–500 mg of hyaluronic acid (sodium hyaluronate) reduces inflammation. The hyaluronic acid enhances the effect of the ascorbic acid. It is thought that this enhanced activity eliminates the free radicals by acting as a free radical scavenger.

A similar situation occurs with the NSAIDS. As a major amount of soluble indomethacin is required, the chemical product was solubilized using n-methyl glucamine at a dilution of 5 mg/ml of n-methyl glucamine (NMG). This substance is then passed through a 22 micron Milipore filter to produce sterility. This material is non-toxic at 16 fold the therapeutic dose in animals and for this reason was considered appropriate to be used in human conditions. Thus, Indocid™ solubilized in NMG is administered to human patients intravenously or intravascularly at a varying dose up to 10 mg/kg where each dose of indomethacin is combined with for example 200–1000 mg of hyaluronic acid (for example "LifeCore™" hyaluronic acid [sodium hyaluronate]) diluted in the original solution of indomethacin and NMG with for example the "LifeCore™" hyaluronic acid. This produces an appropriate mixture and can be administered safely by any of the routes. [Similar clinical studies have been done with hyaluronic acid prepared by other methods, i.e. extraction. The extracted material is satisfactory to use for intravenous.]

Thus when an NSAID for example indomethacin (dissolved in n-methyl glucamine) or other NSAID is administered with greater than 200 mg hyaluronic acid for 1–2 mg/kg body weight of the NSAID (in one instance indomethacin and NMG), no major toxic side effects occur such as gastro-intestinal distress, neurological abnormalities, depression, etc., even at elevated amounts of indomethacin (if necessary). If the amount of hyaluronic acid is decreased below about that amount, the usual side effects may begin to reoccur. In addition, the responses that have been observed are superior when the NSAID (for example Indocid™) is combined with hyaluronic acid demonstrating clearly that the combination is now "targeting" to the tissue when administered by the systemic intravenous route. Thus, it has been observed that patients when receiving in addition to other chemicals (for example ascorbic acid [Vitamin C], 50–200 mg NSAID—hyaluronic acid (sodium hyaluronate) (for example indomethacin and hyaluronic acid) experience dramatic relief of pain immediately. Thus Applicants believe that the addition of the NSAID for example with hyaluronic acid (sodium hyaluronate) prevents enzymatic production of prostaglandin synthetase which blocks macrophage functioning. Thus the hyaluronic acid (and salt and other forms) not only enhance the activity of the NSAID but also reduce any side effects and toxicity that is associated with the use of the prostaglandin synthesis inhibitors.

The hyaluronic acid and salts thereof may be utilized at varying doses—10 to 1000 mg/70 kg person. As there is no toxicity, the hyaluronic acid can obviously be administered in a dose excess (for example 3000 mg/70 kg individual) without any adverse effects.

One form of hyaluronic acid and/or salts thereof (for example sodium salt) and homologues, analogues, derivatives, complexes, esters, fragments, and sub units of hyaluronic acid, preferably hyaluronic acid and salts and thereof suitable for use with Applicant's invention is a fraction supplied by Hyal Pharmaceutical Corporation. One such fraction is a 15 ml vial of Sodium hyaluronate 20 mg/ml (300 mg/vial—Lot 2F3). The sodium hyaluronate fraction is a 2% solution with a mean average molecular weight of about 225,000. The fraction also contains water q.s. which is triple distilled and sterile in accordance with the U.S. patent for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and/or sub units of hyaluronic acid, preferably hyaluronic acid and salts thereof may comprise hyaluronic acid and/or salts thereof having the following characteristics:

a purified, substantially pyrogen-free fraction of hyaluronic acid obtained from a natural source having at least one characteristic selected from the group consisting of the following:

i) a molecular weight within the range of 150,000–225,000;

ii) less than about 1.25% sulphated mucopoly-saccharides on a total weight basis;

iii) less than about 0.6% protein on a total weight basis;

iv) less than about 150 ppm iron on a total weight basis;

v) less than about 15 ppm lead on a total weight basis;

vi) less than 0.0025% glucosamine;

vii) less than 0.025% glucuronic acid;

viii) less than 0.025% N-acetylglucosamine;

ix) less than 0.0025% amino acids;

x) a UV extinction coefficient at 257 nm of less than about 0.275;

xi) a UV extinction coefficient at 280 nm of less than about 0.25; and xii) a pH within the range of 7.3–7.9. Preferably the hyaluronic acid is mixed with water and the fraction of hyaluronic acid fraction has a mean average molecular weight within the range of 150,000–225,000. More preferably the fraction of hyaluronic acid comprises at least one characteristic selected from the group consisting of the following characteristics:

i) less than about 1% sulphated mucopolysaccharides on a total weight basis;

ii) less than about 0.4% protein on a total weight basis;

iii) less than about 100 ppm iron on a total weight basis;

iv) less than about 10 ppm lead on a total weight basis;

v) less than 0.00166% glucosamine;

vi) less than 0.0166% glucuronic acid;

vii) less than 0.0166% N-acetylglucosamine;

viii) less than 0.00166% amino acids;

x) a UV extinction coefficient at 257 nm of less than about 0.23;

xi) a UV extinction coefficient at 280 nm of less than 0.19; and xii) a pH within the range of 7.5–7.7

Other forms of hyaluronic acid and/or its salts, and homologues, derivatives, complexes, esters, fragments and sub units of hyaluronic acid may be chosen from other suppliers. Applicants propose the use of sodium hyaluronate produced and supplied by LifeCore™ Biomedical, Inc. having the following specifications

| Characteristics | Specification |
|---|---|
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |
| Heavy Metals, maximum ppm | |
| As  Cd  Cr  Co  Cu | Fe  Pb  Hg  Ni |
| 2.0  5.0  5.0  10.0  10.0 | 25.0  10.0  10.0  5.0 |
| Microbial Bioburden | None observed |
| Endotoxin | <0.07 EU/mg NaHy |
| Biological Safety Testing | Passes Rabbit Ocular Toxicity Test |

Applicants also propose the use of forms of hyaluronic acid described in the prior art.

The following references teach hyaluronic acid, sources thereof and processes of the manufacture and recovery thereof.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 cm$^3$/g., and preferably greater than about 2000 cm$^3$/g.;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree–cm$^2$/mole (of disaccharide) measured at 220 nanometers;

(f) no significant cellular infiltration of the vitreous and anterior chamber, no flare in the aqueous humor, no haze or flare in the vitreous and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

A Where high molecular weight hyaluronic acid (or salts or other forms thereof) is used, it must be diluted to permit administration and ensure no coagulation or interference with body function.

One formulation of Ascorbic Acid (Vitamin C) injection U.S. patent is manufactured by Steris Laboratories, Inc., Phoenix, Ariz., 85043 U.S.A. and comprises 22 mg/ml (equivalent to sodium ascorbate 250 mg/ml) in 30 ml, 50 ml, or 100 ml individual containers, 30 ml size being preferred.

BRIEF DESCRIPTION OF THE DRAWINGS

Surgical procedures were undertaken to illustrate an embodiment of the invention and analysis of results are illustrated in the enclosed Figures in which;

FIGS. 1A–1D contain photographs of injured and sham operated arteries.

BRIEF DESCRIPTION OF THE EMBODIMENT

The following experiments were conducted.

10 rabbits were anesthetized and balloon angioplasty was performed on them. The rabbits were perfused with hyaluronan (5 mg/ml) or buffer alone and allowed their recovery. Rabbits were sacrificed at 2, 24, 48 hours after injury and carotid arteries were processed for histology and serial 5–10 μm sections were taken for processing. Sections were stained with hematoxylin or with anti RHAMM antibodies. 10 sections of each treatment were analyzed.

The results of the analysis is described below with respect to the Figures.

FIG. 1: Injured carotid arteries show denudating of the endothelio cell layer and adherence of white cells (FIG. 1A). White cells stained positively for RHAMM relative to IgG control background (FIG. 1B). Carotid arteries that were exposed to hyaluronan (FIG. 1C) or sham operated arteries (FIG. 1D) show intact endothelial cell layer and do not exhibit accumulations of white cells.

Figure 2:
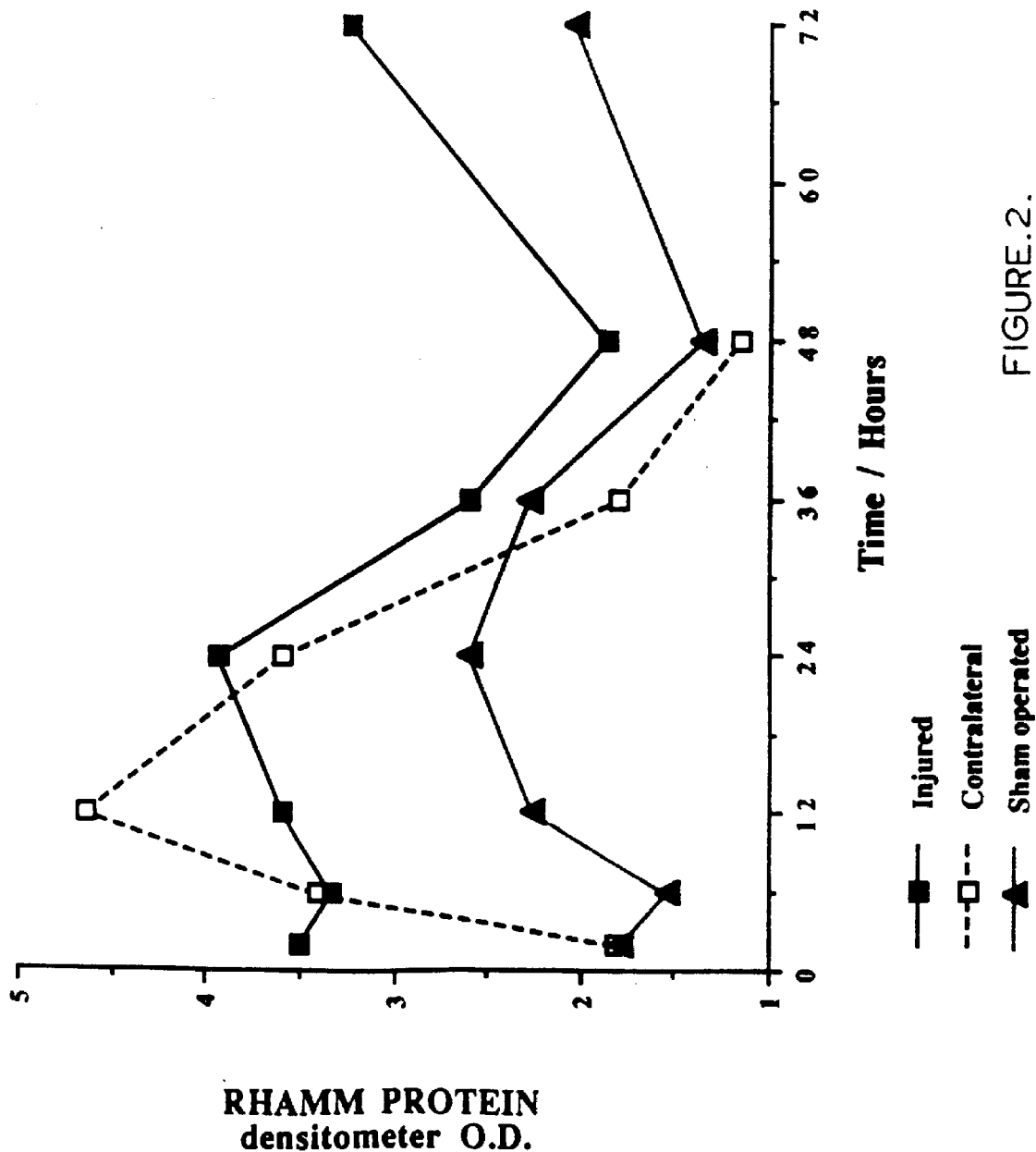
FIG. 2 illustrates in graph form RHAMM (Receptor for HA (Hyaluronan) Mediated Motility) expression by the carotid arteries.

FIG. 2: Western transblot analysis of RHAMM expression by carotid arteries. Carotid arteries were homogenized, the released proteins were electrophoresed on SDS-PAGE and the presence of RHAMM was detected with a mono-specific antibody. The presence of the antibody was visualized with chemiluminescence and the relative amounts of bound antibody were quantified with optical densitometry. Operated animals displayed an acute, large rapid increase in the presence of RHAMM. Levels of RHAMM had dropped by 5–6 days after tissue injury. Sham operated animals showed no increase in RHAMM expression.

Figure 3A:
FIGS. 3A–3C contain photographs of RHAMM and hyaluronan expression in smooth muscle cells of the carotid artery 4 days after their injury.
Figure 3B:
Figure 3C:
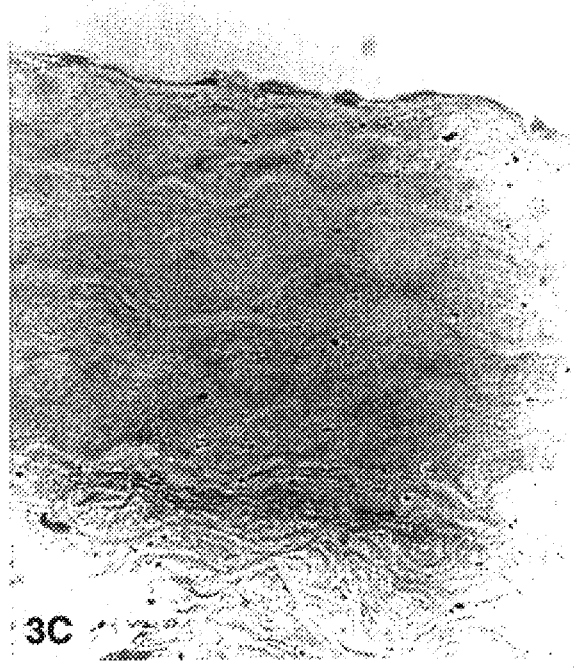

FIG. 3: RHAMM (FIG. 3A) and hyaluronan (FIG. 3B) expression in smooth muscle cells of the carotid artery 4 days after their injury. RHAMM expression on white cells elevated immediately (FIG. 1) while RHAMM expression on smooth muscle cells was increased later and concomitant with the initiation of their locomotion. Smooth muscle cells of sham operated animals did not show a similar increase in the expression of RHAMM (FIG. 3C).

Figure 4:
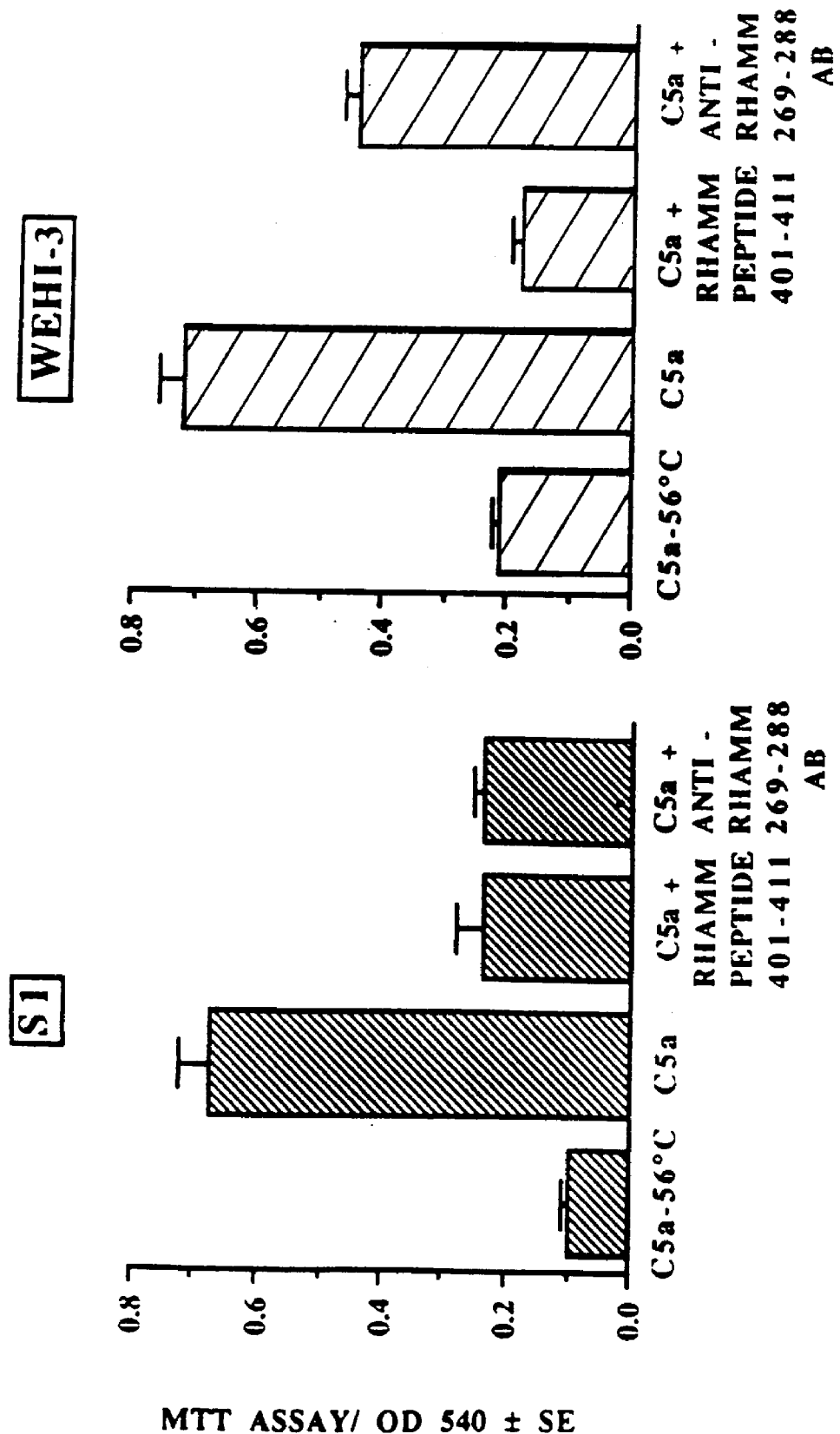
FIG. 4 illustrates in a bar graph the effect of RHAMM, HA binding [Hyaluronan-(Hyaluronic Acid)- binding] peptides (401–411) and anti-Rhamm antibody on the Chemotaxis of Macrophage cell lines to complement (C5a).

FIG. 4: The effect of RHAMM peptides on chemotaxis of neutrophiles in response to IL-8. RHAMM peptides that mimic the hyaluronan binding domain of RHAMM inhibit the chemotaxis of neutrophiles in a Boyden chamber assay.

Figure 5:
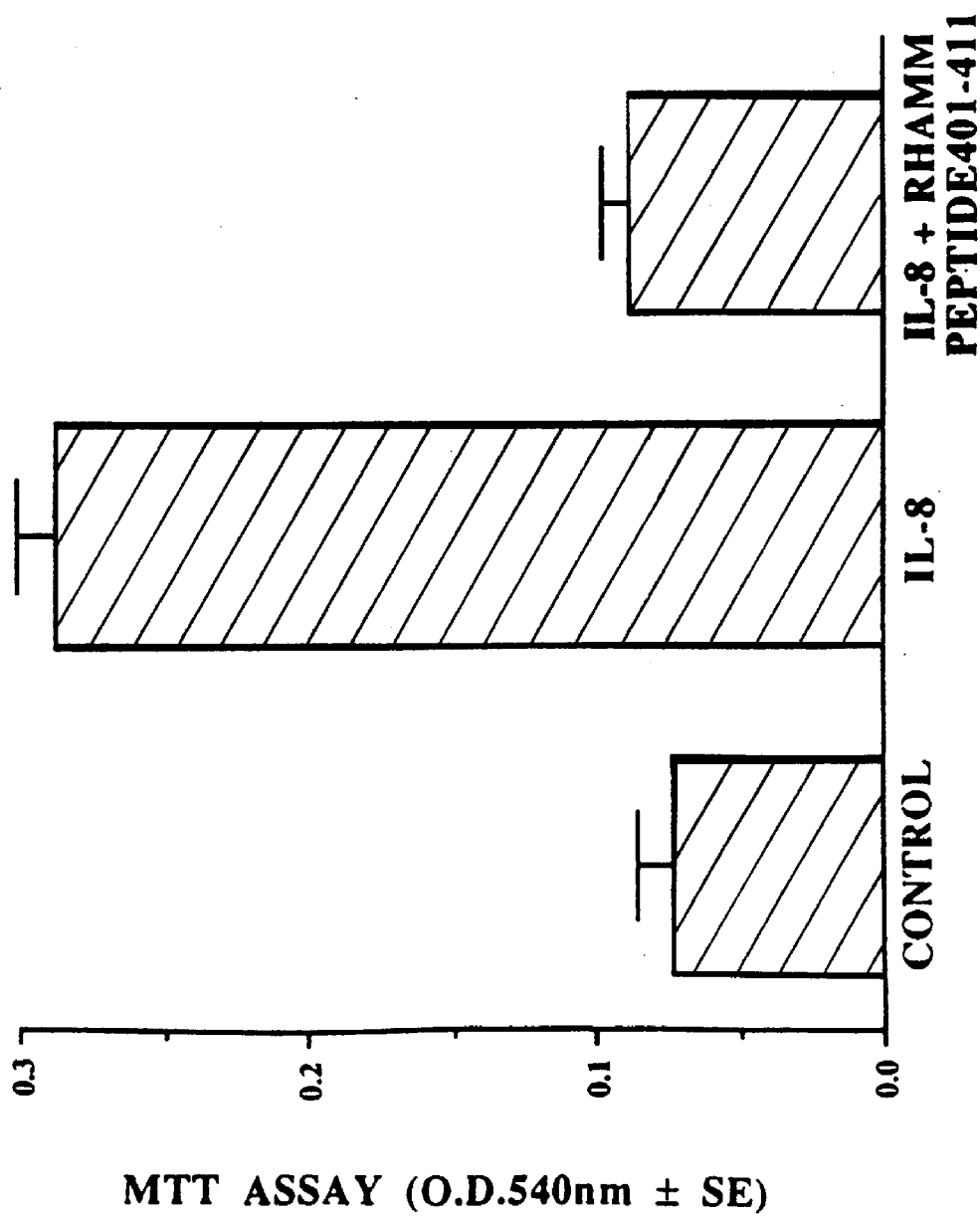
FIG. 5 illustrates in bar graph form the effect of RHAMM HA-Binding peptides (401–411) of the chemotaxis of the neutrophiles to IL-8.

FIG. 5: RHAMM peptides and antibodies inhibit chemotaxis of macrophage cells lines (S1, WEHI-3) in response to complement. Complement but not heat-inactivated complement (56° C.) stimulated chemotaxis of macrophage cell lines. RHAMM peptides that mimic hyaluronan binding domain of RHAMM and anti-RHAMM antibodies inhibit chemotaxis.

Figure 6:
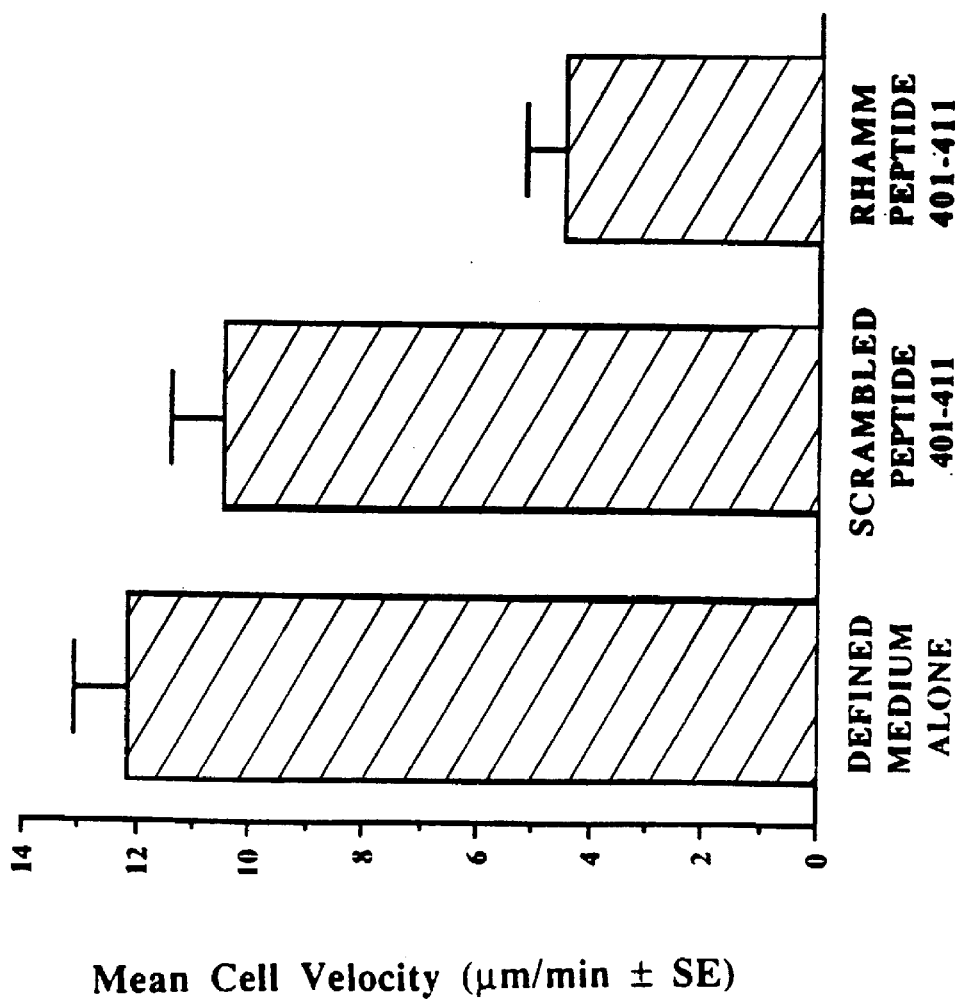
FIG. 6 illustrates in bar graph form the effect of RHAMM HA-binding peptide 401–411 on smooth muscle cell migration 5 hours after wounding.

FIG. 6: RHAMM peptides inhibit the locomotion of smooth muscle cells responding to injury. The RHAMM peptide that mimics the hyaluronan binding domain of RHAMM inhibits the locomotion of injury smooth muscle cells. The scrambled peptide had no effect indicating the specificity to the "sense" peptide.

RHAMM expression (determined by a method of detection named Western transblot analysis using mono-specific antibodies to RHAMM (Turley, e.A., Austin, L., Vandeligt, K. and Clary, C., 1991, J. Cell Biol., 112:1041), revealed an acute increase in expression of this receptor that was detectable by two hours (FIG. 2), a time frame during which white cells were observed in control animals to adhere to the endothelium (FIG. 2). [For a further discussion of RHAMM see the article "Identification of Two Hyaluronan-binding Domains in the Hyaluronan Receptor RHAMM", Baihua Yang, Liying Zhang, and Eva Ann Turley, The Journal of Biological Chemistry, Vol. 268, No. 12, Issue of April 25, pp. 8617–8623, 1993.] RHAMM was also increased in the contralateral artery suggesting the release of a soluble factor that regulates RHAMM expression from the injured tissue. However, sham operated animals showed little increase in the expression of RHAMM (FIG. 2). In experimental animals, expression of RHAMM was maintained for several days, then levels dropped. Examination of fixed tissue revealed that the major cells expressing RHAMM were activated white cells and smooth muscle cells (FIGS. 1, 3). The involvement of RHAMM in white cell and smooth muscle cell locomotion was assessed in vitro using image analysis to measure random locomotion and Boyden chambers to measure chemotaxis. Peptides (100 ng/plate) that mimic regions (in particular the hyaluronan binding domains) of RHAMM, inhibit macrophage (FIG. 4) neutrophiles (FIG. 5) and smooth muscle cell (FIG. 6) migration to a highly significant degree (p>0.0001, Student's "T" test). Collectively, these results indicate that RHAMM, and in particular its Hyaluronan binding capability, is essential for locomotion of white cells and smooth muscle cells and that its expression is elevated at the site of tissue injury following experimental balloon catherization in rabbits.

Hyaluronan treatment of rabbits just prior to their injury abolished adherence of white cells to endothelium resulting in tissue that appeared intact as detected by histological criteria (FIG. 1). Several days after injury, carotid arteries of hyaluronan treated rabbits appeared similar to controls displaying an intact endothelium.

The rationale for these results is that hyaluronan bound to cells expressing high levels of its receptor, RHAMM and prevented subsequent interactions of these cells with the endothelium. It is expected, that expression of the other hyaluronan receptor, CD44, is also elevated.

For a discussion and illustration of terms and expressions in this application, reference should be had to the enclosed unpublished article attached as "Schedule A" entitled "Neointimal Formation after Balloon Catheter Injury: A Role of Hyaluronan and the Hyaluronan Receptor RHAMM", the portions thereof which discuss and illustrate terms and expressions referred to herein are incorporated herein by reference.

As many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A method of inhibiting arterial restenosis in a human in need thereof, comprising administering by perfusion or injection to said human, (a) a therapeutically effective, non-toxic amount of hyaluronic acid and/or a pharmaceutically acceptable salt thereof, and (b) a therapeutically effective amount of one or more agents selected from the group consisting of a non-steroidal anti-inflammatory drug (NSAID), vitamin C, a stenosis inhibiting drug, an anti-oxidant, and a free radical scavenger, wherein the hyaluronic acid and/or pharmaceutically acceptable salt thereof has a molecular weight less than 750,000 daltons and greater than 150,000 daltons.

2. The method of claim 1 wherein the administering is done before, during, or after balloon angioplasty.

3. The method of claim 1 wherein the hyaluronic acid and/or pharmaceutically acceptable salt thereof is administered in an amount between about 10 mg and about 3000 mg.

4. A method of inhibiting arterial restenosis following balloon angioplasty in a human in need thereof, comprising administering by perfusion or injection to said human, (a) a therapeutically effective, non-toxic amount of hyaluronic acid and/or a pharmaceutically acceptable salt thereof, (b) a stenosis inhibiting drug, and (c) a therapeutically effective amount of one or more agents selected from the group consisting of a non-steroidal anti-inflammatory drug (NSAID), vitamin C, an anti-oxidant, and a free radical scavenger, wherein the hyaluronic acid or pharmaceutically acceptable salt thereof has a molecular weight less than 750,000 daltons and greater than 150,000 daltons.

5. The method of claim 4 wherein the hyaluronic acid and/or pharmaceutically acceptable salt thereof is administered in an amount between about 10 mg and about 3000 mg.

6. The method of any of claims 1, 2, or 4 or wherein sodium hyaluronate is administered intravenously.

7. A method of inhibiting arterial restenosis following balloon angioplasty in a human in need thereof, comprising administering by perfusion or injection to said human, (a) a therapeutically effective, non-toxic amount of hyaluronic acid and/or a pharmaceutically acceptable salt thereof, and (b) a therapeutically effective amount of one or more agents selected from the group consisting of a non-steroidal anti-inflammatory drug (NSAID), vitamin C, a stenosis inhibiting drug, an anti-oxidant, and a free radical scavenger, wherein the hyaluronic acid or pharmaceutically acceptable salt thereof has a molecular weight less than 750,000 daltons and greater than 150,000 daltons, and wherein the hyaluronic acid and/or pharmaceutically salt thereof is administered in an amount between about 10 mg and about 3000 mg.

8. The method of claim 7 wherein the hyaluronic acid and/or pharmaceutically acceptable salt thereof and the agent(s) are administered intravenously.

9. The method of claim 7 wherein the agent is a stenosis inhibiting drug.

10. The method of claim 7 wherein the amount of the hyaluronic acid and/or pharmaceutically salt thereof is greater than about 200 mg and is less than about 3000 mg.

* * * * *